United States Patent
Mao et al.

(10) Patent No.: US 11,504,324 B2
(45) Date of Patent: Nov. 22, 2022

(54) NANOSUSPENSION FORMULATION

(71) Applicant: DUPONT NUTRITION USA, INC., Wilmington, DE (US)

(72) Inventors: Shirui Mao, Shenyang (CN); Jian Guan, Shenyang (CN); Trond Helgerud, Lier (NO); Yeli Zhang, Princeton, NJ (US)

(73) Assignee: DUPONT NUTRITION USA, INC., Wilmington, DE (US)

( * ) Notice: Subject to any disclaimer, the term of this patent is extended or adjusted under 35 U.S.C. 154(b) by 412 days.

(21) Appl. No.: 15/525,173

(22) PCT Filed: Nov. 18, 2015

(86) PCT No.: PCT/US2015/061327
§ 371 (c)(1),
(2) Date: May 8, 2017

(87) PCT Pub. No.: WO2016/081593
PCT Pub. Date: May 26, 2016

(65) Prior Publication Data
US 2018/0250227 A1   Sep. 6, 2018

Related U.S. Application Data

(60) Provisional application No. 62/081,834, filed on Nov. 19, 2014.

(51) Int. Cl.
| | | |
|---|---|---|
| A61K 9/10 | (2006.01) |
| A61K 31/366 | (2006.01) |
| A61K 9/20 | (2006.01) |
| A61K 9/16 | (2006.01) |
| A61K 31/351 | (2006.01) |
| A61K 31/496 | (2006.01) |
| A61K 47/36 | (2006.01) |

(52) U.S. Cl.
CPC .............. *A61K 9/10* (2013.01); *A61K 9/1623* (2013.01); *A61K 9/1652* (2013.01); *A61K 9/2018* (2013.01); *A61K 9/2054* (2013.01); *A61K 9/2077* (2013.01); *A61K 31/351* (2013.01); *A61K 31/366* (2013.01); *A61K 31/496* (2013.01); *A61K 47/36* (2013.01)

(58) Field of Classification Search
CPC combination set(s) only.
See application file for complete search history.

(56) References Cited

FOREIGN PATENT DOCUMENTS

| WO | 0015198 A1 | 3/2000 |
| WO | 2013098841 A1 | 7/2013 |

OTHER PUBLICATIONS

Sule (Enhancement of Drug Solubility in Supramolecular and Colloidal System, Journal of Pharmaceutical Sciences, vol. 98, No. 2, Feb. 2009).*

Van Eerdenbrugh, et al., "A Screening Study of Surface Stabilization during the Production of Drug Nanocrystals", Journal of Pharmaceutical Sciences, 2009, vol. 98, No. 6, pp. 2091-2103.

* cited by examiner

*Primary Examiner* — Kathrien A Cruz

(57) ABSTRACT

A nanosuspension comprising (a) a pharmaceutical active ingredient or nutraceutical active ingredient having low solubility; (b) at least one alginate selected from the group consisting of (i) sodium alginate having a viscosity of 100 mPa·s or less in a 1% solution in water at 20° C. and (ii) potassium alginate; and (c) water. Also, a drug dosage form prepared from such a nanosuspension.

17 Claims, No Drawings

NANOSUSPENSION FORMULATION

FIELD OF THE INVENTION

In one aspect, the present invention is directed to a nanosuspension comprising: (a) a pharmaceutical active ingredient or nutraceutical active ingredient having low solubility; (b) at least one alginate selected from the group consisting of (i) sodium alginate having a viscosity of 100 mPa·s or less in a 1% solution in water at 20° C. and (ii) potassium alginate; and (c) water. In another aspect the present invention is directed to a pharmaceutical or nutraceutical dosage form prepared from such a nanosuspension.

BACKGROUND OF THE INVENTION

One major problem associated with drugs which exhibit low solubility is their low bioavailability. Such low bioavailability can be enhanced by formulating such materials as nanosuspensions. Nanosuspensions are formulations in which a poorly soluble drug is suspended in a dispersion without any matrix material. As is noted by Patel et al, *Nanosuspension: An approach to enhance solubility of drugs*, J. Adv. Pharm Technol. Res. 2011 April-June; 2(2); 81-87, nanosuspensions have the advantages that they enhance the dissolution and therefore the bioavailability of drugs; can achieve a higher drug loading; permit a possible dose reduction; and can enhance the physical and chemical stability of drugs.

In forming stable nanosuspensions, it is necessary to consider two aspects of stabilization: (a) the stabilization of the drug surface so as to prevent the drug particles from agglomerating; and (b) the wetting of the particles so that they remain in suspension. The type and amount of stabilizers employed has a pronounced effect upon the physical stability and the in vivo behavior of nanosuspensions.

It would be desirable to possess a nanosuspension which showed desirable physical stability but which employed reduced amounts of a stabilizer. It has now been unexpectedly found that the use of a low molecular weight sodium alginate and/or of a potassium alginate will provide both (a) desirable stabilization in nanosuspensions of poorly soluble drugs; coupled with (b) desirable dissolution profiles when such nanosuspensions are formulated into drug dosage forms; when employed in concentrations much lower than those typically employed for other nanosuspension stabilizers.

SUMMARY OF THE INVENTION

In one aspect, the present invention is directed to a nanosuspension comprising: (a) a pharmaceutical active ingredient or nutraceutical active ingredient having low solubility; (b) at least one alginate selected from the group consisting of (i) sodium alginate having a viscosity of 100 mPa·s or less in a 1% solution in water at 20° C. and (ii) potassium alginate; and (c) water.

In another aspect, the present invention is directed to a pharmaceutical or nutraceutical dosage form produced from such a nanosuspension.

DETAILED DESCRIPTION OF THE INVENTION

In one aspect, the present invention is directed to a nanosuspension comprising: (a) a pharmaceutical active ingredient or nutraceutical active ingredient having low solubility; (b) at least one alginate selected from the group consisting of (i) sodium alginate having a viscosity of 100 mPa·s or less in a 1% solution in water at 20° C. and (ii) potassium alginate; and (c) water.

As is employed herein, the term "pharmaceutical active ingredient having low solubility" means a drug which is classified as a Class II or Class IV active under the Biopharmaceutical Classification System. Pursuant to such Classification System, a drug substance is considered to have low solubility when the highest dose strength is not soluble in 250 mL of water over a pH range of 1 to 7.5. In one embodiment, solubility can be determined according to the parameters set forth in the following matrix at 20° C.:

| Solubility in Water | Parts of water solvent required for 1 part of solute | Solubility range in water (mg/mL) |
| --- | --- | --- |
| Very Soluble | <1 | ≥1000 |
| Freely Soluble | from 1 to 10 | 100-1000 |
| Soluble | from 10 to 30 | 33-100 |
| Sparingly Soluble | from 30 to 100 | 10-33 |
| Slightly Soluble | from 100 to 1000 | 1-10 |
| Very Slight Soluble | from 1000 to 10,000 | 0.1-1 |
| Practically Insoluble | ≥10,000 | <0.1 |

For the purposes of the present invention, a pharmaceutical active ingredient having low solubility includes any drug that falls into the categories: very slightly soluble, and practically insoluble as set forth in the above matrix, although the formulation method described in this invention could increase a drug that falls into the categories sparingly soluble and slightly soluble into one of the more soluble categories described above.

As is employed herein, the terms "pharmaceutical active ingredient" includes veterinary drugs as well as those intended for human use. The term "nutraceutical active ingredient having low solubility" refers to a nutraceutical compound which meets the solubility criteria for a low solubility drug defined above.

The low solubility pharmaceutical active ingredient may be at least one selected, for example, from: a nonsteroidal anti-inflammatory drug including acetaminophen, acetylsalicylic acid, ibuprofen, fenbuprofen, fenoprofen, flurbiprofen, indomethacin, naproxen, etodolac, ketoprofen, dexibuprofen, piroxicam or aceclofenac; an immunosuppressant or atopic dermatitis drug including cyclosporin, tacrolimus, rapamycin, mycophenolate or pimecrolimus; a calcium channel blocker including nifedipine, nimodipine, nitrendipine, nilvadipine, felodipine, amlodipine or isradipine; an angiotensin II antagonist including valsartan, eprosartan, irbesartan, candesartan, telmisartan, olmesartan or losartan; a cholesterol synthesis-inhibiting hypolipidemic agent including atorvastatin, lovastatin, simvastatin, fluvastatin, rosuvastatin or pravastatin; a cholesterol metabolism- and secretion-promoting hypolipidemic agent including gemfibrozil, fenofibrate, etofibrate or bezafibrate; an antidiabetic drug including pioglitazone, rosiglitazone or metformin; a lipase inhibitor including orlistat; an antifungal agent including itraconazole, amphotericin B, terbinafine, nystatin, griseofulvin, fluconazole or ketoconazole; a hepatoprotective drug including biphenyl dimethyl dicarboxylate, silymarin or ursodeoxycholic acid; a gastrointestinal drug including sofalcone, omeprazole, pantoprazole, famotidine, itopride or mesalazine; an antiplatelet agent including cilostazol or clopidogrel; an osteoporosis drug including raloxifene; an antiviral drug including acyclovir, famciclovir, lamivudine or oseltamivir; an antibiotic including clarithromycin, ciprofloxacin or cefuroxime; an antiasthmatic or antihistamine drug including pranlukast, budesonide or fexofenadine; a hormone drug including testosterone, prednisolone, estrogen, cortisone, hydrocortisone or dexamethasone; an anticancer drug including paclitaxel, docetaxel, paclitaxel derivatives, doxorubicin, adriamycin, daunomycin, camptothecin, etoposide, teniposide or busulfan; salts thereof; and pharmaceutical derivatives thereof. Specifically, it may be at least one selected from naproxen, tacrolimus, valsartan, simvastatin, fenofibrate, itraconazole, lovastatin, biphenyl dimethyl dicarboxylate, silymarin, sofalcone, pantoprazole, cilostazol, salts thereof and pharmaceutical derivatives thereof.

It is noted that while several other alginate salts are commercially available, only sodium alginate has monographs in the National Formulary (NF) and European Pharmacopoeia, as well as a Type IV Drug Master File on file with the U.S. Food and Drug Administration. The sodium alginates which may be employed in the compositions of this invention possess a viscosity of 100 mPa·s or less when measured at 1% in water at 20° C. using Brookfield type RV (e.g. RVT, RVF, RVTDV) with Brookfield RV spindle 2. Preferably, such alginates will exhibit a viscosity of less than 75 mPa·s, more preferably of less than 50 mPa·s when so measured. The (1,4)β-D-mannuronate ("M") and (1,4)α-L-guluronate ("G") content of the sodium alginate employed is not particularly critical.

The potassium alginate which may be employed in the composition preferably possesses a viscosity of less than 500 mPa·s when measured in water at 1% at 20° C. using Brookfield type RV (e.g. RVT, RVF, RVTDV) with Brookfield RV spindle 2, although potassium alginates having a higher viscosity may be employed provided that they do not interfere with the drying (particularly spray drying if this method is employed) of the nanosuspension.

The nanosuspensions of this invention typically comprise between 0.1 and 10 percent by weight of the pharmaceutical active ingredient or nutraceutical active ingredient having low solubility. Preferably, such nanosuspensions comprise between 0.5 and 5 percent by weight of the pharmaceutical active ingredient or nutraceutical active ingredient having low solubility, more preferably between 0.5 and 3 percent by weight of the pharmaceutical active ingredient or nutraceutical active ingredient having low solubility, although these percentages may vary depending upon the particular poorly soluble drug selected.

Such nanosuspensions typically comprise between 0.1 and 20 weight percent alginate, based upon the weight of the pharmaceutical active ingredient or nutraceutical active ingredient having low solubility. Preferably, such nanosuspensions comprise between 0.25 and 5 percent by weight of alginate, more preferably between 0.35 and 2 percent by weight, based upon the weight of the pharmaceutical active ingredient or nutraceutical active ingredient having low solubility.

The nanosuspensions may further comprise additional ingredients, for example, protective colloids such as mannitol which are added when the nanosuspension is to be spray dried into a flowable powder.

The particles of the pharmaceutical active ingredient or nutraceutical active ingredient having low solubility in the nanosuspension typically exhibit a particle size distribution of from 10 to 1,000 nm, preferably of from 10 to 400 nm, for 10 to 90% of the particles determined based on a particle size normal distribution curve.

The nanosuspensions of this invention may be produced by any method conventionally employed to produce nanosuspensions. These methods include "bottom up technology", an assembly method to form nanoparticles such as precipitation, microemulsion and melt emulsification; as well as "top down" processes which involve the disintegration of larger particles into nanoparticles, such as high pressure homogenization and milling methods. Such methods are described in Patel et al, cited above.

Preferably, such nanosuspensions are produced via high pressure homogenization. This technique typically involves a three step process in which a powder is dispersed in a stabilizer solution to form a presuspension; the presuspension is homogenized employing a high pressure homogenizer at low pressure; and is then homogenized at high pressure until the nanosuspension is formed with the desired particle size.

A solid composition may be prepared by drying the nanosuspensions described above. Such drying may be achieved by conventional processes including spray drying, freeze drying, vacuum drying or hot air drying. When spray drying is employed, a protective colloid such as mannitol is typically added to the nanosuspension prior to drying.

The present disclosure further provides a pharmaceutical or nutraceutical drug dosage form comprising the powder prepared according to the present disclosure together with a commonly employed pharmaceutically acceptable carrier. Such drug dosage form may be a granule, powder, syrup, liquid, suspension, tablet, capsule, troche or pill for oral administration, or transdermal agent, lotion, ophthalmic ointment, ointment, plaster, cataplasm, cream, paste, suspension, liquid, injection or suppository for parenteral administration. Such drug dosage form may additionally comprise excipients which are conventionally employed in pharmaceutical compositions, and may be prepared by methods familiar to one of ordinary skill in the art.

Typical excipients which may be employed in the drug dosage forms of this invention include fillers and lubricants. These excipients are employed in conventional amounts which are well known to one of ordinary skill in the art.

Suitable fillers include calcium carbonate (Barcroft, Cal-Carb, CalciPure, Destab, MagGran, Millicarb, Pharma-Carb, Precarb, Sturcal, Vivapres Ca), calcium phosphate, dibasic anhydrous (A-TAB, Di-Cafos A-N, Emcompress Anhydrous, Fujicalin), calcium phosphate, dibasic dihydrate (Cafos, Calipharm, Calstar, Di-Cafos, Emcompress), calcium phosphate tribasic (Tri-Cafos, TRI-CAL WG, TRI-TAB), calcium sulphate (Destab, Drierite, Snow White, Cal-Tab, Compactrol, USG Tena Alba), cellulose powdered (Arbocel, Elcema, Sanacel, Solka-Floc), silicified microcrystalline cellulose (ProSolv), cellulose acetate, compressible sugar (Di-Pac), confectioner's sugar, dextranes (Candex, Emdex), dextrin (Avedex, Caloreen, Crystal Gum, Primogran W), dextrose (Caridex, Dextrofin, Lycadex PF, Roferose, Tab fine D-100), fructose (Advantose, Fructamyl, Fructofin, Krystar), kaolinLion, Sim 90), lactitol (Finlac ACX, Finlac DC, Finlac MCX)5 lactose (Aero Flo 20, Aero Flo 65, Anhydrox, CapsuLac, Fast-Flo, FlowLac, GranuLac, InhaLac, Lactochem, Lactohale, Lactopress, Microfine, Microtose, Pharmatose, Prisma Lac, Respitose, SacheLac, SorboLac, Super-Tab, Tablettose, Wyndale, Zeparox), magnesium carbonate, magnesium oxide (MagGran MO), maltodextrin (C*Dry MD, Glucidex, Glucodry, Lycatab DSH, Maldex, Maltagran, Maltrin, Maltrin QD, Paselli MD 10 PH, Star-Dri), maltose (Advantose 100), mannitol (Mannogem, Pearlitol), microcrystalline cellulose (Avicel PH, Celex, Celphere, Ceolus KG, Emcocel, Ethispheres, Fibrocel, Pharmacel, Tabulose, Vivapur), polydextrose (Litesse), simethicone (Dow Corning Q7-2243 LVA, Cow Corning Q7-2587, Sentry Simethicone), sodium alginate (Kelcosol, Keltone, Protanal), sodium chloride (Alberger), sorbitol (Liponec 70-NC, Liponic 76-NC, Meritol, Neosorb, Sorbifin, Sorbitol Instant, Sorbogem), starch (Aytex P, Fluftex W, Instant Pure-Cote, Melojel, Meritena Paygel 55, Perfectamyl D6PH, Pure-Bind, Pure-Cote, Pure-Dent, Pure-Gel, Pure-Set, Purity 21, Purity 826, Tablet White), pregelatinized starch (Instastarch, Lycatab C, Lycatab PGS, Merigel, National 78-1551, Pharma-Gel, Prejel, Sepistab ST 200, Spress B820, Starch 1500 G, Tablitz, Unipure LD, Unipure WG220), sucrose, trehalose and xylitol (Klinit, Xylifm, Xylitab, Xylisorb, Xylitolo).

The term 'filler' is sometimes used interchangeably with the term 'diluent'. However, the term 'filler' is generally used for solid formulations whereas the term 'diluent' is used in liquid formulations.

Suitable lubricants include calcium stearate (HyQual), glycerine monostearate (Capmul GMS-50, Cutina GMS, Imwitor 191 and 900, Kessco GMSS Lipo GMS 410, 450 and 600, Myvaplex 600P, Myvatex, Protachem GMS-450, Rita GMS, Stepan GMS, Tegin, Tegin 503 and 515, Tegin 4100, Tegin M, Unimate GMS), glyceryl behenate (Compritol 888 ATO), glyceryl palmitostearate Precirol ATO 5), hydrogenated castor oil (Castorwax, Castorwax MP 70, Castorwax MP 80, Croduret, Cutina HR, Fancol, Simulsol 1293), hydrogenated vegetable oil type I (Akofine, Lubritab, Sterotex, Dynasan P60, Softisan 154, Hydrocote, Lipovol HS-K, Sterotex HM), magnesium lauryl sulphate, magnesium stearate, medium-chain triglycerides (Captex 300, Captex 355, Crodamol GTC/C, Labrafac CC, Miglyol 810, Miglyol 812, Myritol, Neobee M5, Nesatol, Waglinol 3/9280), poloxamer (Lutrol, Monolan, Pluronic, Supronicm Synperonic), polyethylene glycol (Carbowax, Carbowax Sentry, Lipo, Lipoxol, Lutrol E, Pluriol E), sodium benzoate (Antimol), sodium chloride (Alberger), sodium lauryl sulphate (Elfan 240, Texapon K1 2P), sodium stearyl fumarate (Pruv), stearic acid (Crodacid E570, Emersol, Hystrene, Industrene, Kortacid 1895, Pristerene), talc (Altaic, Luzenac, Luzenac Pharma, Magsil Osmanthus, Magsil Star, Superiore), sucrose stearate (Surfhope SE Pharma D-1803 F) and zinc stearate (HyQual).

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

EXAMPLES

The following Examples are provided to illustrate the invention in accordance with the principles of this invention, but are not to be construed as limiting the invention in any way except as indicated in the appended claims.

Example 1

Preparation of Lovastatin Nanosuspensions

Lovastatin nanosuspensions were prepared by a high pressure homogenization method employing a piston-gap high pressure homogenizer AH100D (ATS Engineering Inc., Shanghai, China). Coarse drug powder (0.5% w/v, 250 mg) was dispersed into an aqueous solution (50 mL) containing 1.25 mg (0.5% based upon the weight of the drug) of the alginate or other stabilizer being evaluated. The coarse suspensions produced were then circulated at 100, 200, 500 and 800 bar for two cycles, followed by several cycles at 1300 bar.

The stabilizers evaluated and their properties are as follows:

| Stabilizer | State | G Content | Viscosity mPa · s in 1% solution |
|---|---|---|---|
| Protanal LFR 5/60 | Sodium Salt | 65-75% | 3.5-7 |
| Protanal CR8133 | Sodium Salt | 37-40 | 15-45 |
| Kelcoloid K3B426 | Esterified (50-60%) Propylene glycol | 37-40 | 50-100 |
| Protanal CR8223 | Sodium salt | 37-40 | 300-450 |

The mean particle size (Z-ave) and polydispersity index (PI) of the nanosuspensions produced were measured by photon correlation spectroscopy using a Malvern Zetasizer Nano ZS 90 (Malvern Instruments, Worcestershire, UK). 100 µL of the nanosuspension was diluted with 3 mL of distilled water and then measured at 25° C. at a scattering angle of 90°. The average of three replicates is summarized in Table 1 below:

TABLE 1

| Sample Number | Alginate | Particle Size (nm) | PI |
|---|---|---|---|
| 1 | Protanal LFR 5/60 | 431.4 | 0.398 |
| 2 | Protanal CR8133 | 399.0 | 0.273 |
| A | Protanal CR8223 | 383.4 | 0.321 |
| B | Kelcoloid K3B426 | 407.3 | 0.333 |

Example 2

Influence of Alginate LFR5/60 Concentration on Particle Size of Lovastatin Nanosuspension Employing the method and apparatus described in Example 1, several nanosuspensions of lovastatin were prepared employing varying amounts of Alginate LFR5/60. The particle size and PI of such suspensions was measured as described in Example 1. The results of such evaluation are summarized in Table 2 below.

TABLE 2

| Concentration Stabilizer/Drug (w/w) | Particle Size (nm) | PI |
|---|---|---|
| 0.50% | 431.4 | 0.398 |
| 1% | 367.8 | 0.323 |
| 5% | 378.1 | 0.327 |
| 10% | 472.5 | 0.482 |
| 20% | 500.1 | 0.366 |
| 30% | 608.9 | 0.519 |
| 40% | 657.0 | 0.536 |

Example 3

Influence of Alginate CR8133 Concentration on Particle Size of Lovastatin Nanosuspension Employing the method and apparatus described in Example 1, several nanosuspensions of lovastatin were prepared employing varying amounts of Protanal CR8133. The particle size and PI of such suspensions was measured as described in Example 1. The results of such evaluation are summarized in Table 3 below.

TABLE 3

| Concentration Stabilizer/Drug (w/w) | Particle Size (nm) | PI |
|---|---|---|
| 0.10% | 431.6 | 0.397 |
| 0.50% | 399.0 | 0.273 |
| 1% | 456.9 | 0.344 |
| 5% | 552.8 | 0.440 |

Example 4

Comparison of Low Viscosity Alginates and Other Commonly Used Stabilizers in Lovastatin Nanosuspensions Several nanosuspensions were prepared (by the high pressure homogenization method described in Example 1) employing the following stabilizers commonly used to produce nanosuspensions of lovastatin. The following stabilizers were employed at a 20% concentration of stabilizer/drug (w/w), in contrast to the alginates which were employed at much lower concentrations:

HPMC=hydroxypropyl methyl cellulose HPMC 2910E3 (Shin Etsu)
K30=polyvinylpyrrolidone Kollidon 30(BASF)
K17=polyvinylpyrrolidone Kollidon 17 (BASF)
K12=polyvinylpyrrolidone Kollidon 12 (BASF)
PVA=polyvinyl acetate
F68=poloxamer Pluronic F68 (BASF)
F127=poloxamer Pluronic F127 (BASF)
SDS=sodium dodecyl sulfate The particle size of such compositions was measured as set forth in Example 1. The results of such testing are summarized in Table 4 below:

TABLE 4

| Stabilizer | Concentration | Particle Size (nm) |
|---|---|---|
| LFR 5/60 | 1% | 367.8 |
| CR 8133 | 0.5% | 399.0 |
| HPMC | 20% | 434.3 |
| K30 | 20% | 374.4 |
| K17 | 20% | 362.0 |
| K12 | 20% | 394.5 |
| PVA | 20% | 471.6 |
| F68 | 20% | 421.5 |
| F127 | 20% | 444.8 |
| SDS | 20% | 493.0 |

The above results show that low viscosity sodium alginates produce nanosuspensions having particle sizes equivalent to those produced by conventionally employed stabilizers at much higher concentrations.

Example 5

Preparation of Itraconazole Nanosuspensions

Employing the equipment described in Example 1, itraconazole nanosuspensions were prepared as follows. Coarse drug powder (0.5% w/v, 250 mg) was dispersed into an aqueous solution (50 mL) containing 1.25 mg (0.5% based upon the weight of the drug) of the alginate or other stabilizer being evaluated. The coarse suspensions produced were then circulated at 100, 200, 500 and 800 bar for two cycles, followed by several cycles at 1300 bar.

The mean particle size (Z-ave) and polydisersity index (PI) of the nanosuspensions produced were measured by photon correlation spectroscopy using a Malvern Zetasizer Nano ZS 90 (Malvern Instruments, Worcestershire, UK). 100 µL of the nanosuspension was diluted with 3 mL of distilled water and then measured at 25° C. at a scattering angle of 90°. The average of three replicates is summarized in Table 3 below:

TABLE 5

| Sample Number | Alginate | Particle Size (nm) | PI |
|---|---|---|---|
| 3 | Protanal LFR 5/60 | 439.4 | 0.423 |
| 4 | Protanal CR8133 | 516.7 | 0.665 |
| C | Protanal CR8223 | 474.8 | 0.557 |

Example 6

Influence of Alginate LFR5/60 Concentration on Particle Size of Itraconazole Nanosuspension Employing the method and apparatus described in Example 5, several nanosuspensions of itraconazole were prepared employing varying amounts of Alginate LFR5/60. The particle size and PI of such suspensions was measured as described in Example 5. The results of such evaluation are summarized in Table 6 below.

TABLE 6

| Concentration Stabilizer/Drug (w/w) | Particle Size (nm) | PI |
|---|---|---|
| 0.50% | 439.4 | 0.423 |
| 1% | 483.6 | 0.569 |
| 5% | 461.6 | 0.456 |
| 10% | 474.4 | 0.558 |

Example 7

Stability of Lovastatin:LFR 5/60 Nanosuspensions

Sample of the 1% nanosuspension of Example 2 were stored at 4° C. and 25° C. and the particle size and PI measured daily as described in Example 1. The results of such testing are summarized in Table 7 below:

TABLE 7

| | 4° C. Storage | | 25° C. Storage | |
|---|---|---|---|---|
| Time (Days) | Particle Size (nm) | PI | Particle Size (nm) | PI |
| 0 | 396.7 | 0.38 | 396.7 | 0.38 |
| 1 | 396.8 | 0.41 | 396.7 | 0.38 |
| 2 | 385.8 | 0.27 | 384.7 | 0.27 |
| 3 | 413.1 | 0.32 | 416.5 | 0.33 |
| 4 | 407.1 | 0.34 | 413.2 | 0.34 |
| 5 | 423.1 | 0.34 | 421.2 | 0.37 |
| 6 | 401.2 | 0.28 | 412.0 | 0.29 |

Example 8

Stability of Itraconazole:LFR 5/60 Nanosuspension

Samples of the 1% nanosuspension of Example 6 were stored at 25° C. and the particle size and PI was measured after 6 days as described in Example 5. The results of such testing are summarized in Table 8 below.

TABLE 8

| Time (Days) | Particle Size (nm) | PI |
|---|---|---|
| 0 | 439.4 | 0.42 |
| 6 | 502.6 | 0.58 |

Example 9

Dissolution Study of Lovastatin:Alginate Drug Forms

A. Spray Drying of Lovastatin:Alginate Nanosuspensions

Lovastatin:alginate nanosuspensions prepared as described in Example 1 employing the optimized amount of stabilizer concentration (based upon the weight of the lovastatin present) as set forth in Table 10 below. These nanosuspensions were spray dried by initially adding 400% mannitol into the liquid as protective agent followed by spray drying with a laboratory-scale spray dryer (SD 1000, Eyela, Japan) under the following conditions: 100° C. inlet temperature, 60-70° C. outlet temperature, 2.8 mL/min feeding rate, 23 kPa atomization air pressure and 0.65-0.70 m³/min drying air flow rate. The powder was collected and stored in a desiccator at room temperature.

B. Conversion the Spray Dried Powder into Tablets

The spray dried nanosuspension powders produced in step A above were mixed with those excipients listed in Table 9 to form a mixed powder, then the mixed powder was compressed into tablets having the following composition:

TABLE 9

| Component | Quantity (mg) |
|---|---|
| Lovastatin | 20 |
| Alginate Powder | [as indicated] |
| Mannitol | 80 |
| Ac-Di-Sol | 15 |
| Magnesium stearate | 0.45 |
| Talc | 2.25 |
| Microcrystalline cellulose PH-200 | 32.1 |

C. In Vitro Dissolution Study

An in vitro dissolution study was carried out using the paddle method equipped with a USP II apparatus at 37.5° C. and a paddle speed of 50 rpm. A sample of the nanodispersion (containing 60 mg lovastatin) was added into a 900 mL dissolution medium (0.05M pH6.8 phosphate buffer with 0.1% SDS as non-sink condition). 6 mL samples were periodically collected and immediately filtered through a 0.15 µm syringe filter. The first two mL of filtrate was discarded, and the remaining filtrate collected for analysis at 237 nm using a UV spectrophotometer (UV-2000, UNIC Instrument Corp., Shanghai, China). An equal volume of fresh dissolution medium was added. The study was conducted in triplicate, and the average results are included in Table 10 below.

TABLE 10

| Sample (Concentration) | Accumulated Release Percent | | | |
|---|---|---|---|---|
| | 5 Minutes | 10 Minutes | 15 Minutes | 30 Minutes |
| LFR 5/60 (1.0%) | 79.8 | 87.4 | 91.8 | 93.0 |
| CR 8133(0.5%) | 79.3 | 96.5 | 98.5 | 101.9 |
| K3B426(0.5%) | 59.5 | 73.7 | 78.5 | 84.8 |
| CR 8223 (1.0%) | 71.4 | 78.9 | 86.1 | 90.2 |

The results above show that the use of sodium alginates having a lower viscosity results in a more rapid release of lovastatin.

Example 10

Dissolution Study of Itraconazole:Alginate Drug Forms

A. Spray Drying of Itraconazole:Alginate Nanosuspensions

Solid compositions of the itraconazole:alginate nanosuspensions prepared as described in Example 5 were spray dried by initially adding 400% mannitol into the liquid as protective agent followed by spray drying using a Buchi B-290Mini spray dryer at following conditions: inlet temperature: 120° C., outlet temperature: 50-60° C., atomization air pressure: 24 kpa, feeding speed: 2.0 mL/min.

B. Conversion the Spray Dried Powder into Tablets

The spray dried nanosuspension powders produced in step A above were mixed with those excipients listed in Table 11 to form a mixed powder, then the mixed powder was compressed into tablets having the following composition:

TABLE 11

| Component | Quantity (mg) |
|---|---|
| Itraconazole | 50 |
| Protanal LFR5/60 | 0.25 |
| Mannitol | 225 |
| Ac-Di-Sol | 25 |
| Magnesium stearate | 1.5 |
| Talc | 7.5 |
| Microcrystalline cellulose PH-200 | 190.75 |

An in vitro dissolution study was carried out using the paddle method equipped with a USP II apparatus at 37.5° C. and a paddle speed of 50 rpm. A sample of the nanosuspension based tablets (containing 50 mg itraconazole) was added into a 900 mL dissolution medium (0.1M HCl with 0.1% SDS as non-sink condition). 6 mL samples were periodically collected and immediately filtered through a 0.15 µm syringe filter. The first two mL of filtrate was discarded, and the remaining filtrate collected for analysis at 261 nm using a UV spectrophotometer (UV-2000, UNIC Instrument Corp., Shanghai, China). An equal volume of fresh dissolution medium was added. The study was conducted in triplicate, and the average results are included in Table 12 below.

TABLE 12

| | Accumulated Release Percent | | | |
|---|---|---|---|---|
| Sample | 5 Minutes | 10 Minutes | 15 Minutes | 30 Minutes |
| 3 | 32.0% | 43.1% | 53.7% | 58.3% |
| 4 | 41.5% | 49.7% | 55.0% | 58.9% |
| C | 30.8% | 40.1% | 44.0% | 47.9% |

The results above show that the use of sodium alginates having a lower viscosity results in a more rapid release of itraconazole.

Example 11

Comparison of Sodium and Potassium Lovastatin Drug Forms

Employing the process and apparatus described in Example 9, lovastatin drug forms were prepared from nanosuspensions containing 0.5 weight percent KF200FTS (a potassium alginate) or 1.0 weight percent of Protanal CR8133 were produced. The characterization of such alginates is presented in the Table 13 below:

TABLE 13

| Alginate | Protanal CR8133 | KF200FTS |
|---|---|---|
| Salt | Sodium | Potassium |
| Viscosity (1% solution) Pa · S | 300-450 | 200-400 |
| G Content | 37-40 | 60-70 |

The accumulated release percent was measured after 10 minutes employing the method described in Example 9. It was found that the total release of the sodium alginate drug form was 78.8%, whereas the total release from the potassium alginate drug form was 88.1%.

What is claimed is:

1. A nanosuspension comprising (a) a pharmaceutical active ingredient or nutraceutical active ingredient having a solubility of 0.1-1 mg/mL or less than 0.1 mg/mL in water at 20° C. ; (b) at least one alginate selected from the group consisting of (i) sodium alginate having a viscosity of 100 mPa·s or less in a 1% solution in water at 20° C. and (ii) potassium alginate; and (c) water.

2. The nanosuspension of claim 1 wherein the pharmaceutical active ingredient or nutraceutical active ingredient comprises between 0.1 and 10 percent by weight of the nanosuspension.

3. The nanosuspension of claim 2 wherein the pharmaceutical active ingredient or nutraceutical active ingredient comprises between 0.5 and 5 percent by weight of the nanosuspension.

4. The nanosuspension of claim 3 wherein the pharmaceutical active ingredient or nutraceutical active ingredient comprises between 0.5 and 3 percent by weight of the nanosuspension.

5. The nanosuspension of claim 1 wherein the alginate is present in an amount between 0.1 and 20 percent by weight, based upon the weight of the pharmaceutical active ingredient or nutraceutical active ingredient.

6. The nanosuspension of claim 5 wherein the alginate is present in an amount between 0.25 and 5 percent by weight, based upon the weight of the pharmaceutical active ingredient or nutraceutical active ingredient.

7. The nanosuspension of claim 6 wherein the alginate is present in an amount between 0.35 and 2 percent by weight, based upon the weight of the pharmaceutical active ingredient or nutraceutical active ingredient.

8. The nanosuspension of claim 1 wherein the alginate comprises said sodium alginate.

9. The nanosuspension of claim 1 wherein the alginate comprises said potassium alginate.

10. The nanosuspension of claim 9 wherein the potassium alginate has a viscosity of 500 mPa·s or less in a 1% solution in water at 20° C.

11. The nanosuspension of claim 1 wherein the pharmaceutical active ingredient is selected from the group consisting of a nonsteroidal anti-inflammatory drugs, immunosuppressant drugs, atopic dermatitis drugs, calcium channel blockers, angiotensin II antagonists, cholesterol synthesis-inhibiting hypolipidemic agents, cholesterol metabolism- and secretion-promoting hypolipidemic agents, antidiabetic drugs, lipase inhibitors, antifungal agents, hepatoprotective drugs, gastrointestinal drugs, antiplatelet agents, osteoporosis drugs, antiviral drugs, antibiotics, antiasthmatic or antihistamine drugs, hormone drugs and anticancer drugs.

12. The nanosuspension of claim 1 wherein the pharmaceutical active ingredient is selected from the group consisting of acetaminophen, acetylsalicylic acid, ibuprofen, fenbuprofen, fenoprofen, flurbiprofen, indomethacin, naproxen, etodolac, ketoprofen, dexibuprofen, piroxicam, aceclofenac, cyclosporin, tacrolimus, rapamycin, mycophenolate, pimecrolimus, nifedipine, nimodipine, nitrendipine, nilvadipine, felodipine, amlodipine, isradipine, valsartan, eprosartan, irbesartan, candesartan, telmisartan, olmesartan, losartan, atorvastatin, lovastatin, simvastatin, fluvastatin, rosuvastatin, pravastatin, gemfibrozil, fenofibrate, etofibrate, bezafibrate, pioglitazone, rosiglitazone, metformin, orlistat, itraconazole, amphotericin B, terbinafine, nystatin, griseofulvin, fluconazole, ketoconazole, biphenyl dimethyl dicarboxylate, silymarin ursodeoxycholic acid, sofalcone, omeprazole, pantoprazole, famotidine, itopride, mesalazine, cilostazol, clopidogrel, raloxifene, acyclovir, famciclovir, lamivudine, oseltamivir, clarithromycin, ciprofloxacin, cefuroxime, pranlukast, budesonide, fexofenadine, testosterone, prednisolone, estrogen, cortisone, hydrocortisone, dexamethasone, docetaxel, paclitaxel derivatives, doxorubicin, adriamycin, daunomycin, camptothecin, etoposide, teniposide and busulfan; and pharmaceutical derivatives and salts thereof.

13. A pharmaceutical or nutraceutical dosage form produced from the nanosuspension of claim 1.

14. The nanosuspension of claim 8 wherein the sodium alginate has a viscosity of 75 mPa·s or less in a 1% solution in water at 20° C.

15. The nanosuspension of claim 8 wherein the sodium alginate has a viscosity of 50 mPa·s or less in a 1% solution in water at 20° C.

16. The nanosuspension of claim 1 wherein particles of the pharmaceutical active ingredient or nutraceutical active ingredient have a particle size distribution of from 10 to 1,000 nm for 10 to 90% of the particles determined based on a particle size normal distribution curve.

17. The nanosuspension of claim 1 wherein particles of the pharmaceutical active ingredient or nutraceutical active ingredient have a particle size distribution of from 10 to 400 nm for 10 to 90% of the particles determined based on a particle size normal distribution curve.

\* \* \* \* \*